United States Patent [19]

Corti et al.

[11] Patent Number: 5,114,978
[45] Date of Patent: May 19, 1992

[54] ANHYDROUS BLENDS OF P-CHLORO-M-XYLENOL IN SURFACTANT MIXTURES

[75] Inventors: Mike E. Corti, New Egypt, N.J.; Richard R. Tenore, North East, Md.

[73] Assignee: Rhone-Poulenc Surfactants and Specialties, L.P., Princeton, N.J.

[21] Appl. No.: 596,295

[22] Filed: Oct. 15, 1990

[51] Int. Cl.$^5$ .......................................... A61K 31/055
[52] U.S. Cl. .................................... 514/737; 514/625; 514/716
[58] Field of Search ........................................ 514/737

[56] References Cited

U.S. PATENT DOCUMENTS 2,191,405  2/1940  Hueter et al. .................... 514/737
4,668,419  5/1987  Moseman ........................ 514/737

OTHER PUBLICATIONS

AlcoCare Brochure.

Primary Examiner—Allen J. Robinson
Assistant Examiner—S. Mark Clardy
Attorney, Agent, or Firm—Finnegan, Henderson, Farabow, Garrett & Dunner

[57] ABSTRACT

A composition, or an aqueous mixture containing a composition of a substantially anhydrous blends of parachlorometaxylenol, fatty acid diethanolamides, and anionic surfactants of the class diethanolammonium alkylpolyoxyethyl sulfate and method for making such compositions. The compositions and solutions containing the composition have antimicrobial and cleansing properties.

23 Claims, No Drawings

ANHYDROUS BLENDS OF P-CHLORO-M-XYLENOL IN SURFACTANT MIXTURES

This invention relates to a composition containing parachlorometaxylenol. It also relates to clear concentrated solutions of parachlorometaxylenol. It also relates to a method for solubilizing parachlorometaxylenol in high concentrations in water or aqueous compositions. The invention further relates to less concentrated and dilute solutions made by dissolving the more concentrated solutions in water or aqueous compositions.

BACKGROUND OF THE INVENTION

Parachlorometaxylenol is listed in the Merck Index as 4-chloro-3,5-dimethyl phenol, and is often called PCMX, as it will be referred to hereinafter. The structural formula of PCMX is:

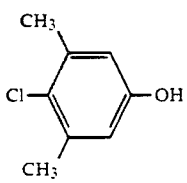

PCMX is a well known antimicrobial compound that has about 60 times the germicidal potency of carbolic acid.

It is practically insoluble in water. Only about one gram of PCMX will dissolve in about 3 liters of water at 20° C. A concentrated solution of PCMX in pure water at ambient temperature contains only about 0.03% of the compound on a weight to weight basis.

At low concentrations up to about 3.75% by weight in any vehicle, PCMX is considered to be relatively non-toxic and non-irritating to human skin. In principle, water should be the best solvent vehicle for applying PCMX in solution to human skin since it is the least toxic and least irritating to humans, and produces the fewest deleterious side effects.

Therefore, aqueous solutions of PCMX should be the best liquid for adding PCMX to such products as cosmetics, toiletries, personal care products, surgical scrubs, and items which are applied to human skin.

However, because of its low solubility in water, it has been difficult or impossible heretofore to prepare aqueous compositions containing PCMX in germicidally effective concentrations of about 0.5% or above.

Adding a water soluble solvent such as ethanol or acetone to water or aqueous compositions does permit higher concentrations of PCMX in the solvent vehicle. But a low concentration of organic solvent in water or aqueous compositions does not increase appreciably the solubility of PCMX. Furthermore, since organic solvents irritate human skin, aqueous compositions containing higher concentrations of an organic solvent are of questionable value in such consumer products as cosmetics, toiletries, and personal care items which must remain on the skin for considerable periods of time after application.

High concentrations of organic solvents present additional problems in manufacturing because of their volatility and flammability.

In the past, higher concentrations of PCMX have been prepared by making oil-in-water emulsions or dispersions. In such preparations, PCMX is dissolved almost entirely in the oil phase. But in such two phase systems, the anti-microbial activity of PCMX depends on its concentration in the aqueous phase. Therefore the germicidal properties of an emulsion having a PCMX component is relatively very low with respect to its PCMX content.

Aqueous compositions containing higher concentrations of PCMX have been prepared in the past with the aid of water soluble non-ionic surfactants having polyoxyethyl chains. In these surfactant-water systems, the solubility of PCMX appears to be proportional to the concentration of non-ionic surfactants (J. PHARM. AND PHARMACOL. 8 774-80, 1956). However, it has been shown that non-ionic surfactants reduce considerably the germicidal effectiveness of lipophilic PCMX in aqueous vehicles (CA 73 288412g, and CA 73 28843 h). Therefore, in order to obtain the desired antimicrobial effectiveness of aqueous compositions containing both PCMX and a non-ionic surfactant, higher concentrations of PCMX would be required. This, in turn, would require higher concentrations of non-ionic surfactant until the concentration of PCMX delivers the required antimicrobial activity.

However, it is well known that non-ionic surfactants can produce irritation in humans, especially if left on the skin for extended periods of time. Therefore, the combination of a non-ionic surfactant and a higher concentration of PCMX would increase the amount of skin irritation when used together as components of cosmetics, toiletries, personal care products, and surgical scrubs.

In view of the fact that PCMX is not soluble enough in water to prepare aqueous solutions of high enough concentration to be practical as antimicrobials, it would be a significant advance in the art to find a way of increasing the solubility of PCMX in aqueous media without attenuating its antimicrobial properties, and without adding components which irritate human skin. It would also be useful to be able to prepare compositions or concentrated solutions of PCMX that are completely soluble in aqueous media so that they can be diluted easily to yield clear aqueous solutions of PCMX of desired concentration with a high degree of germicidal activity and a low degree of skin irritability.

SUMMARY OF THE INVENTION

The present invention provides a composition which forms a clear, concentrated solution which is water soluble in all proportions. The present invention also provides a concentrated solution having great economic utility because of the savings in storage space, shipping charges, and manufacturing costs in general.

The present invention further provides an easy and uncomplicated way of introducing parachlorometaxylenol into an aqueous system when products having even low concentrations of parachlorometaxylenol might otherwise be difficult or impossible to prepare.

The compositions and solutions provided in the present invention are useful in many industries in which intermediate materials or final products require antimicrobial properties or cleansing properties, or both. They are especially useful in the manufacture of cosmetics, toiletries, personal care products, and surgical scrubs.

In one embodiment, the present invention provides a composition that forms a clear, homogeneous solution with water in all proportions comprising a substantially anhydrous mixture of a blend of parachlorometaxylenol, diethanolamides of fatty acids, and anionic surfactants of the class diethanolammonium salts of alkylpolyoxyethylsulfuric acid.

In another embodiment, the present invention provides an aqueous solution comprising a composition that forms a clear, homogeneous solution with water in all proportions comprising a substantially anhydrous mixture of a blend of parachlorometaxylenol, diethanolamides of fatty acids, and anionic surfactants of the class diethanolammonium salts of alkylpolyoxyethylsulfuric acid.

In another embodiment, the present invention provides a method of making a clear homogeneous blend of parachlorometaxylenol that forms a clear, homogeneous solution with water in all proportions comprising the steps of:

(a) making a solution of a mixture of fatty acid diethanolamides and diethanolamine;

(b) adding to this solution a mixture of an alkylpolyoxyethylsulfuric acid of the formula:

$$R^1 (OCH_2CH_2)_n OSO_3H$$

wherein $R^1$ represents saturated or unsaturated alkyl groups having an average chain length of 8 to 18 carbon atoms, and n is an integer having an average value of from 0 to 12, at a rate at which the exothermic reaction temperature is maintained below 45° C.; and (c) adding parachlorometaxylenol to this mixture with stirring.

DETAILED DESCRIPTION OF THE INVENTION

In a preferred embodiment, the present invention provides a substantially anhydrous mixture or blend of PCMX, diethanolamides of fatty acids, and anionic surfactants of the class diethanolammonium salts of alkylpolyoxyethylsulfuric acid which form clear, concentrated solutions which are water soluble in all proportions.

It is surprising that combination of the present invention provides a soluble solution because if the three components of the mixture are added one at a time to water in any order, PCMX will remain insoluble, even if the aqueous mixture is stirred and heated for an extended period of time. The reason for this unexpected water solubility of PCMX after it is blended or mixed with diethanolamides of fatty acids, and anionic surfactants of the class diethanolammonium alkylpolyoxyethylsulfate is not certain. Schmulbach (J. Org. Chem. 29 3122-4, 1964, 1964) and Jösten (J. Am. Chem. Soc. 84 2696-9) have disclosed thermodynamic data for complex formation between phenols and amides. Aside from the fact that PCMX was not studied, and only low molecular weight amides were used in these studies, all of the experiments were carried out in carbon tetrachloride solvent, not in water. Furthermore, no products were isolated, so it was not established whether the complexes (if actual) were water soluble or whether they were soluble in aqueous solutions of anionic surfactant.

The parachlorometaxylenol, diethanolamides of fatty acids and anionic surfactants of the class diethanolammonium salts of alkylpolyoxyethylsulfuric acid can be combined in any amount in accordance with the claimed invention. Generally, the parachlorometaxylenol is present in an amount ranging from about 5 to about 25 percent, by weight, the diethanolamides of fatty acids are present in an amount ranging from about 40 to about 65 percent, by weight, and the anionic surfactants of the class diethanolammonium salts of alkylpolyoxyethylsulfuric acid are present in an amount ranging from about 25 to about 45 percent, by weight.

In one preferred embodiment, the parachlorometaxylenol is present at an amount ranging from about 7 to about 23 percent, by weight, said diethanolamides of fatty acids are present at an amount ranging from about 43 to about 61 percent, by weight, and said anionic surfactants of the class diethanolammonium salts of alkylpolyoxyethylsulfuric acid are present at an amount ranging from about 27 to about 42 percent by weight.

The diethanolamides of the fatty acids of the present invention can be selected from at least one of the compounds having the formula:

$$R-\overset{O}{\underset{\|}{C}}-N(CH_2CH_2OH)_2$$

wherein

$$R-\overset{O}{\underset{\|}{C}}$$

represents that portion of the fatty acids of formula

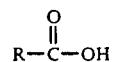
$$R-\overset{O}{\underset{\|}{C}}-OH$$

that are found in the glyceride esters of vegetable oils. These acids may be saturated or unsaturated, or may have a hydroxyl substituent.

The most common fatty acids found in vegetable oils are:

caproic, which has 6 carbon atoms;
caprylic, which has 8 carbon atoms;
capric, which has 10 carbon atoms;
lauric, which has 12 carbon atoms;
myristic, which has 14 carbon atoms;
palmitic, which has 16 carbon atoms;
stearic, which has 18 carbon atoms;
oleic and linoleic, which have 18 carbon atoms and are unsaturated; and
ricinoleic, which has 18 carbon atoms, is unsaturated and has a hydroxyl substituent.

Diethanolamides of fatty acids of this invention are made by the well known method of treating a vegetable oil with diethanolamine, and they are available for purchase in the open market. Any diethanolamide of fatty acid or combination of diethanolamides of fatty acids can be used in the present invention.

For economic and other considerations, the fatty acid diethanolamides derived from coconut oil are the amides of choice. Coconut oil generally has the following acids and amounts, by weight:

0.5% caproic acid;
7 % caprylic acid;
6 % capric acid;
48% lauric acid;
19% myristic acid;
9 % palmitic acid;
3 % stearic acid;
6 % oleic acid; and
1.5% linoleic acid.

Diethanolamides of fatty acids derived from other vegetable oils or synthetic versions of these acids are also within the scope of this invention.

The diethanolamides of single fatty acids, instead of mixtures found in vegetable oils, may also be used. However, single diethanolamides do not permit as high a concentration PCMX in the amide-anionic surfactant blend as do the mixtures of amides. When the single diethanolamide of stearic, or palmitic acid was used in the blend, PCMX was soluble only to the extent of about 6% by weight. Therefore, amide mixtures are preferred.

The anionic surfactants of the class diethanolammonium of alkylpolyoxyethyl sulfate of the present invention generally have the formula:

$$R^1 (OCH_2CH_2)_n O SO_3^- N^+ H_2 (CH_2CH_2OH)_2$$

They are salts made by neutralizing the alkylpolyoxyethylsulfuric acid of formula $R^1 (OCH_2CH_2)_n OSO_3H$ with a slight molar excess of diethanolamine of the formula $HN(CH_2CH_2OH)_2$.

In these formulas $R^1$ stands for saturated or unsaturated alkyl groups having from about 6 to 18 carbon atoms, and preferably from about 10 to 14 carbon atoms, most preferably about 12 carbon atoms, and "n" is an integer of from about zero to 12, preferably from about 0 to 4, and most preferably about 3.

The alkylpolyoxyethylsulfuric acids are made by the well known reaction between the alkylpolyoxyethyl alcohols of formula $R^1 (OCH_2CH_2)_n OH$ with chlorosulfonic acid of the formula $ClSO_2OH$.

The alkylpolyoxyethyl alcohols are available for purchase in the market as non-ionic surfactants.

The non-ionic alkylpolyoxyethyl alcohols generally available in the market are actually mixtures of components. The alkyl group usually is represented as an average of the number of carbon atoms, and the number of oxyethyl groups, "n", is the average of the number of oxyethyl groups in the mixture.

The preferred alkylpolyoxyethyl alcohols used to make the alkylpolyoxyethylsulfuric acids have an average chain length of the alkyl group $R^1$ of about 12 carbon atoms, and the average number of oxyethyl groups is about 3. However, mixtures of alcohols in which the average number of carbon atoms is as low as 6, or as high as 18, and where the average number of oxyethyl groups is zero or as high as 12, are also useful in this invention.

The neutralization of the alkylpolyoxyethylsulfuric acid with diethanolamine is highly exothermic, and often results in a darkening of the anionic surfactant product, even if the reaction mixture is cooled.

It was found that if the neutralization is performed in situ, rather than externally, with agitation, and at a temperatures below 45° C., the light color will be preserved. In this preferred procedure, it is important to add the alkylpolyoxyethylsulfuric acid to a homogenized mixture of fatty acid diethanolamide and diethanolamine. On the other hand, if the diethanolamine is added to a homogenized mixture of amide and acid, a clear solution may not result and the adduct may darken.

The ratio of fatty acid diethanolamide to anionic surfactant can range from about 1:1 to about 9:1. The preferred ratio of fatty acid diethanolamide to anionic surfactant is about 3:2 by weight.

The ratio of diethanolamine to alkylpolyoxyethylsulfuric acid can range from about 1:4 to about 2:3. The preferred ratio of diethanolamine to alkylpolyoxyethylsulfuric acid is 1.5:4 by weight. Therefore, the preferred ratio of amide:amine:acid is 6:1.5:4.

In one preferred procedure, 60 parts by weight of coconut oil fatty acid diethanolamides and 10 parts of diethanolamine were added together at room temperature and thoroughly mixed or homogenized. Then 30 parts of a mixture of alkylpolyoxyethylsulfuric acids of the formula $R^1 (OCH_2CH_2)_n OSO_3H$, wherein the average carbon chain length in $R^1$ was about 12, and the average number of oxyethyl groups was about 3, was dropped slowly into the homogenized mixture with constant stirring, and at a rate to keep the temperature below 45° C., even if external cooling was required. The blend of amides and anionic surfactant had the following properties:

Appearance: Clear may turn hazy upon standing
% Solids: Over 99%
Alkali No: About 96
Color (Gardner): 6
Specific Gravity: 1.04–1.06
Viscosity @25° C.: 1000–2000 cps This blend was utilized to prepare a PCMX concentrate by mixing the blend with the desired proportion of PCMX.

The clear concentrated blend of PCMX, amides, and anionic surfactant is soluble in water in all proportions. With regard to the fatty acid amides, the monoethanol amides are not as effective as the diethanolamides for solubilizing PCMX. With regard to the anionic surfactant, neither the monoethanolammonium nor the triethanolammonium salt is as effective as the diethanolammonium salt for solubilizing PCMX. Single alkylethersulfates and mixtures of alkylethersulfates are equally effective in solubilizing PCMX.

A concentrate containing PCMX when diluted with water to a 1% concentration of PCMX, produced the following one minute bacteria kill, at pH 7–10:

| | |
|---|---|
| Escherichia Coli (EC) | $10^6$ Log Reduction |
| Pseudomonas Aeruginosa (PA) | $10^3$ Log Reduction |
| Staphylococcus Aureus (SA) | $10^6$ Log Reduction |

When the pH was reduced to 5–7 by the addition of citric acid, the following bacteria kill was obtained:

| | |
|---|---|
| Escherichia Coli (EC) | $10^6$ Log Reduction |
| Pseudomonas Aeruginosa (PA) | $10^1$ Log Reduction |
| Staphylococcus Aureus (SA) | $10^5$ Log Reduction |

At 3% concentration of PCMX, the one minute bacteria kill was:

| | | | |
|---|---|---|---|
| EC | 8739 | $10^8$ | $10^6$ Log Reduction |
| PA | 6538 | $10^6$ | $10^6$ Log Reduction |
| SA | 9027 | $10^6$ | $10^6$ Log Reduction |

At any pH between 5 and 9, a 3% concentration of PCMX made by diluting a concentrate will pass the chlorine equivalency test as described in the *OFFICIAL METHODS OF ANALYSIS OF THE ASSOCIATION OF OFFICIAL ANALYTICAL CHEMISTS*, 14th edition, under the title "Chlorine (available) in Disinfectants, Germicidal Equivalent Concentration".

The following examples are meant to illustrate the production and use of the products of this invention. The invention is not limited to the examples that are disclosed but is only limited by the appended claims.

EXAMPLE 1

A mixture of 600 grams of substantially anhydrous liquid diethanolamides derived from the fatty acids in coconut oil (called coco diethanolamide in the industry) and 400 grams of the substantially anhydrous diethanolammonium salt of lauryltrioxyethyl sulfuric acid of the formula:

$$C_{12}H_{25}(OCH_2CH_2)_3\,O\,SO_3^-\,N^-H_2(CH_2CH_2OH)_2$$

wherein 12 was the average number of carbon atoms, and 3 was the average number of oxyethyl groups, was stirred until a clear homogeneous solution resulted.

While stirring this solution, 300 grams of PCMX were added slowly in portions of 10 to 20 grams and the mixture stirred until a clear homogeneous solution resulted. The final solution contained about 46% of the amide mixture, about 31% of the anionic surfactant salt, and about 23% of PCMX. It formed clear solutions with water in all proportions.

EXAMPLE 2

A mixture of 600 grams of substantially anhydrous liquid coco diethanolamide and 100 grams of substantially anhydrous diethanolamine was stirred until a clear homogeneous solution resulted. Then 300 grams of lauryltrioxyethyl sulfuric acid was added in small portions while the mixture was stirred and cooled. The reaction temperature did not exceed 45° C. When the mixture was clear and homogeneous, while stirring constantly, 300 grams of PCMX were added in small portions. The final mixture was a clear homogeneous solution. It contained about 46% of amide, about 31% of anionic surfactant salt, and about 23% of PCMX. It formed clear homogeneous solutions with water in all proportions.

EXAMPLE 3

The procedure in Example 2 was followed except that 70 grams of PCMX were used instead of 300 grams. The final clear solution contained about 56% of amide, about 37% of anionic surfactant, and about 7% of PCMX. It formed clear homogeneous solutions with water in all proportions.

EXAMPLE 4

The procedure in Example 2 was followed except that 550 grams of coco diethanolamide were used instead of 600 grams, 113 grams of diethanolamine were used instead of 100 grams, and 337 grams of lauryltrioxyethyl sulfuric acid were used instead of 300 grams.

The final clear homogeneous solution contained about 43% of amide, about 34% of anionic surfactant, and about 23% of PCMX. It formed clear homogeneous solutions with water in all proportions.

EXAMPLE 5

The procedure in Example 2 was followed except that 650 grams of coco diethanolamide were used instead of 600 grams, 88 grams of diethanolamine were used instead of 100 grams, and 262 grams of lauryltrioxyethyl sulfuric acid were used instead of 300 grams. The final clear homogeneous solution contained about 50% of amide, about 27% of anionic surfactant, and about 23% of PCMX. It formed clear homogeneous solutions with water in all proportions.

EXAMPLE 6

The procedure in Example 3 was followed except that 550 grams of coco diethanolamide were used instead of 600 grams, 113 grams of diethanolamine were used instead of 100 grams, and 337 grams of lauryltrioxyethyl sulfuric acid were used instead of 300 grams.

The final clear homogeneous solution contained about 51% of amide, about 42% of anionic surfactant, and about 7% of PCMX. It formed clear homogeneous solutions with water in all proportions.

EXAMPLES 7

The procedure in Example 3 was followed except that 650 grams of coco diethanolamide were used instead of 600 grams, 88 grams of diethanolamine were used instead of 100 grams, and 262 grams of lauryltrioxyethyl sulfuric acid were used instead of 300 grams. The final clear homogeneous solution contained about 61% of amide, about 32% of anionic surfactant, and about 7% of PCMX. It formed clear homogeneous solutions with water in all proportions.

The above examples demonstrate some of the preferred embodiments of the claimed invention. However, the scope of protection to which the invention is entitled is not limited to these examples, but includes variations which would occur to one of ordinary skill in the art. The scope of the invention is set forth in the following claims.

We claim:

1. A composition that forms a clear, homogeneous solution with water in all proportions comprising a substantially anhydrous mixture of a blend of parachlorometaxylenol, a diethanolamide of a fatty acid, and an anionic surfactant of the class of a diethanolammonium salt of an alkylpolyoxyethylsulfuric acid.

2. The composition of claim 1 wherein the diethanolamide of the fatty acid is selected from at least one of the compounds having the formula:

$$R-\overset{O}{\underset{\|}{C}}-NH-(CH_2CH_2OH)_2$$

wherein $$R-\overset{O}{\underset{\|}{C}}$$

represents that portion of the fatty acid of the formula $$R-\overset{O}{\underset{\|}{C}}-OH$$

that are found in the glyceride esters of a vegetable oil.

3. The composition of claim 2 wherein the fatty acid is selected from at least one of the group consisting of a saturated, unsaturated, and hydroxyl substituted acid.

4. The composition of claim 2 wherein said fatty acid is selected from at least one of the group consisting of caproic, caprylic, capric, lauric, myristic, palmitic, stearic, oleic, linoleic, and ricinoleic acids.

5. The composition of claim 2 wherein the fatty acid diethanolamide is derived from the fatty acid glycerides found in coconut oil.

6. The composition of claim 1 wherein said anionic surfactant of the class of a diethanolammonium salt of an alkylpolyoxyethylsulfuric acid is a mixture of anionic surfactants of the formula:

$$R^1 (OCH_2CH_2)_n O SO_3^- N^- H_2 (CH_2CH_2OH)_2$$

wherein $R^1$ represents a saturated or unsaturated alkyl chain having an average of about 8 to 18 carbon atoms, and n represents an integer having an average value of from 0 to 12.

7. The composition of claim 6 wherein $R^1$ represents a saturated or unsaturated alkyl chain having an average of about 12 carbon atoms, and n represents an integer having an average of about 3.

8. The composition of claim 1 wherein said parachlorometaxylenol is present in an amount ranging from about 5 to about 25 percent, by weight, said diethanolamide of a fatty acid is present in an amount ranging from about 40 to about 65 percent, by weight, and said anionic surfactant of the class of a diethanolammonium salt of an alkylpolyoxyethylsulfuric acid is present in an amount ranging from about 25 to about 45 percent, by weight.

9. The composition of claim 1 wherein said parachlorometaxylenol is present in an amount of about 23 percent, by weight, said diethanolamide of a fatty acid is present in an amount of about 46 percent, by weight, and said anionic surfactant of the class of a diethanolammonium salt of an alkylpolyoxyethylsulfuric acid is present in an amount of about 31 percent by weight.

10. The composition of claim 1 wherein said parachlorometaxylenol is present in an amount of about 7 percent, by weight, said diethanolamide of a fatty acid is present in an amount of about 56 percent, by weight, and said anionic surfactant of the class of a diethanolammonium salt of an alkylpolyoxyethyl-sulfuric acid is present in an amount of about 37 percent by weight.

11. A method of making a clear homogeneous blend of parachlorometaxylenol that forms a clear homogeneous solution with water in all proportions comprising the steps of:
 (a) making a solution of a mixture of a fatty acid diethanolamide and diethanolamine;
 (b) adding to the solution a mixture of alkylpolyoxyethyl sulfuric acids of formula $R^1 (OCH_2CH_2)_n OSO_3H$ wherein $R^1$ represents saturated or unsaturate alkyl groups having an average chain length of 8 to 18 carbon atoms, and n is an integer having an average value of from 0 to 12, at a rate which keeps the exothermic reaction temperature below 45° C.; and
 (c) adding parachlorometaxylenol to the mixture of (a) and (b) with stirring.

12. The method of claim 11 where the ratio of said fatty acid diethanolamide to said mixture of alkylpolyoxyethyl sulfuric acid ranges from about 1:1 to about 9:1.

13. The method of claim 11 where the ratio of said diethanolamine to said mixture of alkylpolyoxyethyl sulfuric acid ranges from about 1:4 to about 2:3.

14. An aqueous solution comprising water and a composition comprising a substantially anhydrous mixture of a blend of parachlorometaxylenol, a diethanolamide of fatty acid, and an anionic surfactant of the class of a diethanolammonium salt of an alkylpolyoxyethylsulfuric acid.

15. The aqueous solution of claim 14 wherein the diethanolamide of the fatty acid has the formula:

$$R-\underset{\underset{O}{\|}}{C}-NH-(CH_2CH_2OH)_2$$

wherein $$R-\underset{\underset{O}{\|}}{C}$$

represents that portion of a fatty acid of the formula $$R-\underset{\underset{O}{\|}}{C}-OH$$

that is found in the glyceride ester of vegetable oil.

16. The aqueous solution of claim 15 wherein the fatty acid is selected from the group consisting of a saturated, unsaturated, and hydroxyl substituted acid.

17. The aqueous solution of claim 15 wherein said fatty acid is selected from at least one of the group consisting of caproic, caprylic, capric, lauric. myristic, palmitic, stearic, oleic, linoleic, and ricinoleic acids.

18. The aqueous solution of claim 15 wherein the fatty acid diethanolamide is derived from the fatty acid glycerides found in coconut oil.

19. The aqueous solution of claim 14 wherein said anionic surfactant of the class of a diethanolammonium salt of an alkylpolyoxyethylsulfuric acid is a mixture of anionic surfactants of the formula:

$$R^1 (OCH_2CH_2)_n O SO_3^- N^- H_2 (CH_2CH_2OH)_2$$

wherein $R^1$ represents saturated or unsaturated alkyl having an average of about 8 to 18 carbon atoms, and n represent an integer having an average value of from 0 to 12.

20. The aqueous solution of claim 19 wherein $R^1$ represents saturated or unsaturated alkyl chains having an average of about 12 carbon atoms, and n represents an integer having an average value of about 3.

21. The aqueous solution of claim 14 wherein said parachlorometaxylenol is present in an amount ranging from about 5 to about 25 percent, by weight, said diethanolamide of fatty acid is present in an amount ranging from about 40 to about 65 percent, by weight, and said anionic surfactant of the class of a diethanolammonium salt of an alkylpolyoxyethylsulfuric acid is present in an amount ranging from about 25 to about 45 percent, by weight.

22. The aqueous solution of claim 14 wherein said parachlorometaxylenol is present in an amount of about 23 percent, by weight, said diethanolamide of fatty acid is present in an amount of about 46 percent, by weight, and said anionic surfactant of the class of a diethanolammonium salt of an alkylpolyoxyethylsulfuric acid is present in an amount of about 31 percent by weight.

23. The aqueous solution of claim 14 wherein said parachlorometaxylenol is present in an amount of about 7 percent, by weight, said diethanolamide of fatty acid is present in an amount of about 56 percent, by weight, and said anionic surfactant of the class of a diethanolammonium salt of an alkylpolyoxyethylsulfuric acid is present at about 37 percent by weight.

* * * * *